United States Patent [19]
Omi et al.

[11] Patent Number: 5,447,640
[45] Date of Patent: Sep. 5, 1995

[54] METHOD AND APPARATUS FOR STERILIZATION OF AND TREATMENT WITH OZONIZED WATER

[75] Inventors: Tadahiro Omi, Miyagi; Makoto Shimada, Tokyo; Isao Sawamoto, Kanagawa, all of Japan

[73] Assignee: Permelec Electrode Ltd., Kanagawa, Japan

[21] Appl. No.: 266,588

[22] Filed: Jun. 28, 1994

[30] Foreign Application Priority Data

Jun. 28, 1993 [JP] Japan .................................. 5-189252
Jun. 30, 1993 [JP] Japan .................................. 5-189251

[51] Int. Cl.$^6$ .............................. C02F 1/46; C02F 1/70; C02F 1/72
[52] U.S. Cl. ..................... 210/748; 210/760; 210/192; 210/259; 210/900
[58] Field of Search ............... 210/760, 900, 748, 259, 210/192

[56] References Cited

U.S. PATENT DOCUMENTS

| | | | |
|---|---|---|---|
| 4,548,716 | 10/1985 | Boeve | 210/652 |
| 4,842,723 | 6/1989 | Parks et al. | 210/192 |
| 4,990,260 | 2/1991 | Pisani | 210/664 |
| 5,073,268 | 12/1991 | Saito et al. | 210/638 |
| 5,114,549 | 5/1992 | Shimamune et al. | 204/149 |
| 5,124,033 | 6/1992 | Ohmi et al. | 210/900 |
| 5,160,429 | 11/1992 | Ohmi et al. | 210/900 |
| 5,190,627 | 3/1993 | Saito et al. | 204/158.2 |
| 5,259,972 | 11/1993 | Miyamaru et al. | 210/900 |

*Primary Examiner*—Cynthia L. Nessler
*Attorney, Agent, or Firm*—Sughrue, Mion, Zinn, Macpeak & Seas

[57] ABSTRACT

Disclosed are a method for treatment with ozonized water which comprises feeding primary pure water to an ultrapure-water producing device containing at least a polisher to convert the primary pure water to ultrapure water, injecting an ozone-containing gas into the ultrapure water to produce ozonized water, sending the ozonized water to a point of use, using the ozonized water for treatment, and circulating the resulting spent ozonized water to the ultrapure-water producing device for reuse or discharging the spent water, wherein the method further comprises supplying a hydrogen-containing gas to the spent ozonized water at a point downstream from the use point to remove residual ozone from the ozonized water, a method for the ozone sterilization of ultrapure water which comprises feeding primary pure water from a primary-pure-water tank to an ultrapure-water producing device containing at least a polisher to convert the primary pure water to ultrapure water, sending the ultrapure water to a use point through a feed line, treating an object with the ultrapure water at the use point, and circulating the resulting spent pure water to the primary-pure-water tank through a return line, which method includes injecting ozone into the spent pure water between the use point and the primary-pure-water tank and supplying a hydrogen-containing gas to the primary pure water between the primary-pure-water tank and the ultrapure-water producing device to conduct residual-ozone removal and oxygen elimination, and apparatuses for use in practicing these methods.

6 Claims, 3 Drawing Sheets

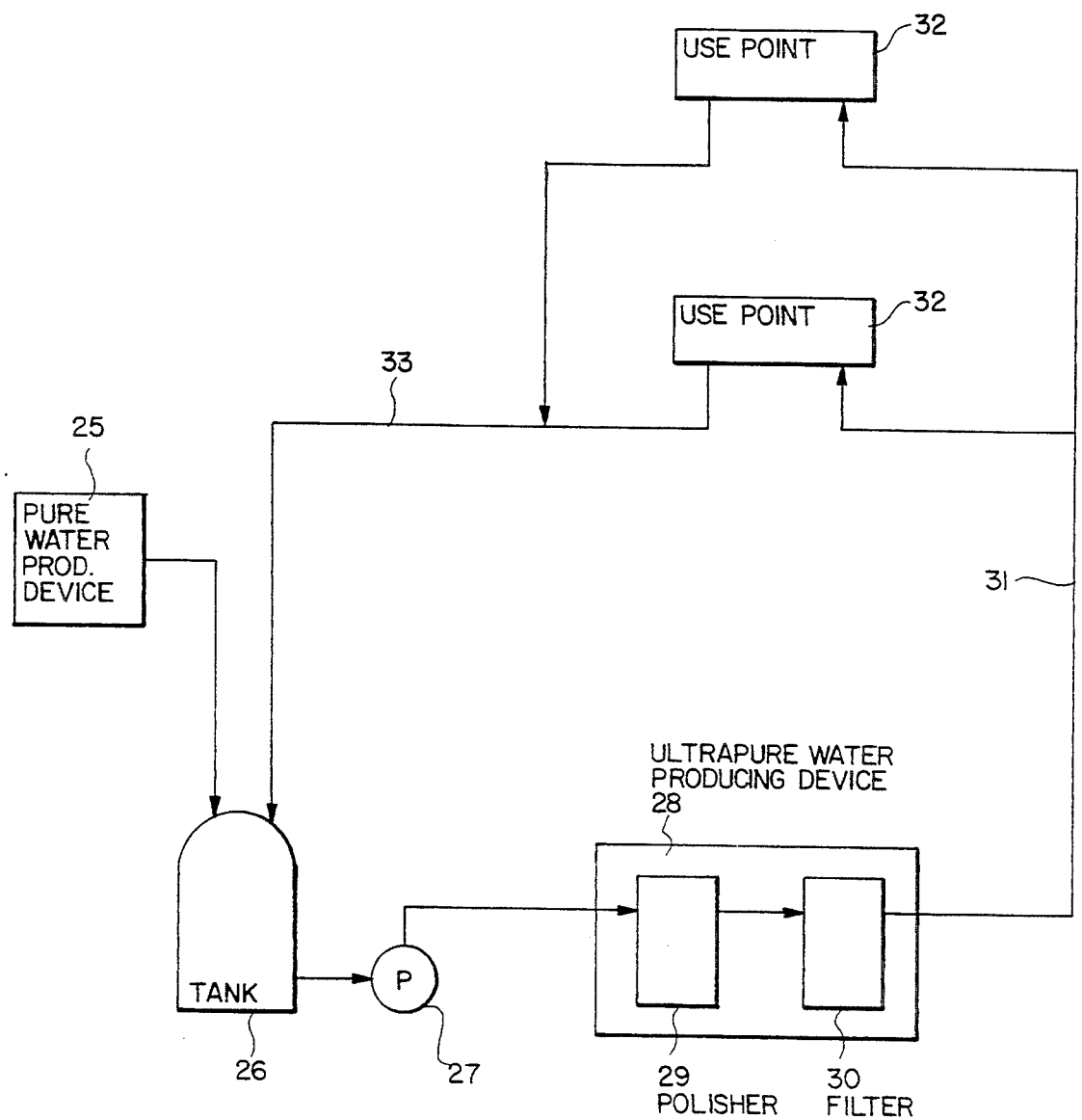

METHOD AND APPARATUS FOR STERILIZATION OF AND TREATMENT WITH OZONIZED WATER

FIELD OF THE INVENTION

The present invention relates to a method and apparatus for treatment with ozonized water. More particularly, the present invention relates to a method and apparatus for efficiently removing ozone from spent ozonized water used for sterilization, cleaning, etc. in technical fields such as the electronics industry, production of pharmaceutical preparations, etc.

The present invention also relates to a method and apparatus for keeping an ultrapure-water supplying system in a highly sterile state which system produces and supplies a large quantity of ultrapure water required in technical fields such as the electronics industry, production of pharmaceutical preparations, etc.

BACKGROUND OF THE INVENTION

In producing ultrapure water required in technical fields such as cleaning of electronic parts in the electronics industry, manufacture of pharmaceutical preparations, etc., pure water produced by primary purification such as distillation or ion exchange is supplied to an ultrapure-water producing device containing a polisher (a well-known device for improving the purity of water, which a resin is packed in) and the like to further remove impurities including particles to thereby improve the purity of the water. The ultrapure water thus produced is fed to a use point through a feed line and is used for cleaning or other purposes. Thereafter, the unused ultrapure water or the spent pure water is circulated to the primary purification step and reused.

Illustratively stated, as shown in FIG. 3, pure water produced in a pure-water producing device 25 and stored in a primary-pure-water tank 26 is sent to an ultrapure-water producing device 28 by means of a pump 27. The ultrapure-water producing device 28 comprises at least a polisher 29 which removes inorganic substances from the pure water and a precision filter 30, e.g., a microfilter or an ultrafiltration membrane, which removes fine particles and organic polymers, and serves to improve the purity of the supplied pure water and filter off the resulting impurities. The ultrapure-water producing device 28 may contain an ultraviolet sterilization lamp for destroying live bacteria. In the case shown in FIG. 3, the ultrapure water produced by the ultrapure-water producing device 28 is fed through a feed line 31 to two use points 32, where a treatment, e.g., cleaning of electronic parts, is conducted. The spent pure water resulting from this treatment or the unused ultrapure water which has not been used in the treatment because of the excess amount fed is collected and circulated to the primary-pure-water tank 26 through a return line 33, and is then resent to the ultrapure-water producing device 28 and reused for cleaning or other purposes.

In this treating system shown in FIG. 3, which is based on the circulation of ultrapure water, the ultrapure water is used effectively and the treatment can be conducted efficiently as described above. However, even when the ultraviolet sterilization lamp is used, the sterilization capability of the lamp is so low that the growth of bacteria is observed even when the circulating pump 27 is operated to maintain the circulatory flow so as to avoid water stagnation. The bacteria deteriorate the quality of the ultrapure water and the treatment with this quality-deteriorated ultrapure water at the use points leads to impaired quality of the resulting treated products and to a decrease in yield or production efficiency. As the number of bacteria thus increases, the number of particles present in the ultrapure water in the system and the TOC (total organic carbon) of the water tend to increase.

Hitherto, the generally employed technique for keeping the number of bacteria which inevitably multiply in the ultrapure-water circulating system at the lowest possible level has been to periodically stop the operation and to add either a germicide, e.g., sodium hypochlorite, hydrogen peroxide and ozone, or hot water to the system, to thereby sterilize and clean the inside of the system.

Although this effective technique is in inhibiting the multiplication of bacteria, this technique is disadvantageous in that it is necessary to stop the operation of the ultrapure-water circulating system for a few hours to one day. Hence, the production of ultrapure water and the manufacturing process employing the ultrapure water must be stopped or slowed down during that period. In particular, in the electronics industry where year-round continuous operation is desired, it is undesirable to employ the above-described technique which leads to a decrease in production efficiency.

Furthermore, the technique of adding a germicide results in secondary problems. For example, it is necessary that after the use of a germicide for the system to be thoroughly post-cleaned with ultrapure water so as to prevent the germicide from remaining in the system, and this post-cleaning causes a problem also in the treatment of the resulting wastewater. In the case of using hot water, there are problems concerning the consumption of heat energy required for heating, the heat resistance of organic and other materials employed in the system piping, etc., which problems remain unsolved.

Further, to improve the efficiency of treatment, e.g., cleaning of parts, an attempt has been to dissolve ozone into the ultrapure water and use this ozone-containing ultrapure water for a treatment such as the cleaning described above.

Ozone has a higher oxidizing power than chlorine, is effective in sterilization, deodorizing, decoloring, etc., and does not pose any problem concerning secondary environmental pollution because it decomposes to oxygen relatively readily after serving its oxidative function. Hence, the range of ozone utilization is expanding recently.

However, the decomposition does not proceed completely, and ozone remains in a slight amount. In addition, the spent ultrapure water also contains oxygen dissolved therein which is the decomposition product. At present, treatment with active carbon is performed in order to completely remove these residual gases before the water is discarded as an effluent. This treatment, however, results in the presence of a large amount of impurities attributable to the active carbon. The amount of impurity is so large that the treated water cannot virtually be returned to the above-described ultrapure-water circulating system and reused. Since residual gases adversely affect the ultrapure-water producing device etc., circulation of the spent pure water which has not been treated to remove gases is not adequate.

In order to eliminate these drawbacks, a technique has been proposed in which the piping is formed of a material unsuited for bacterial growth and a low-pressure ultraviolet ozone decomposer is disposed immediately before the ultrapure-water producing device to conduct ozone decomposition (unexamined published Japanese patent application No. 2144195). However, this technique has the drawback that the complete decomposition of the ozone with a low-pressure ultraviolet ozone decomposer is difficult and ozone remains in the pure water to be fed to the ultrapure-water producing device, with the ultrapure-water producing device tending not to fully exhibit its performance.

SUMMARY OF THE INVENTION

An object of the present invention is to provide a method and apparatus for treatment with ozonized water, by which method and apparatus the problems of the prior art techniques described above are eliminated and the ozone present in the spent pure water used for cleaning or other purposes or present in unused ultrapure water is decomposed substantially completely to enable the resulting water to be discharged or circulated for reuse.

Another object of the present invention is to provide a method and apparatus for ozone sterilization of ultrapure water, by which method and apparatus the problems of the prior art techniques described above are eliminated and the treatment of parts with high-purity ultrapure water can be performed while the number of bacteria present in the ultrapure water in the ultrapure-water producing and supplying system is kept at the lowest level substantially without stopping the operation of the system.

The present invention provides in one embodiment a method for treatment with ozonized water which comprises
- feeding primary pure water to an ultrapure-water producing device containing at least a polisher to convert the primary pure water to ultrapure water,
- injecting an ozone-containing gas into the ultrapure water to produce ozonized water,
- sending the ozonized water to a point of use,
- using the ozonized water for treatment, and
- circulating the resulting spent ozonized water to the ultrapure-water producing device for reuse or discharging the spent water, wherein the method further comprises supplying a hydrogen-containing gas to the spent ozonized water at a point downstream from the use point to remove residual ozone from the ozonized water. This invention further provides an apparatus for use in practicing the method.

The present invention provides in another embodiment a method for the ozone sterilization of ultrapure water which comprises
- feeding primary pure water from a primary-pure-water tank to an ultrapure-water producing device containing at least a polisher to convert the primary pure water to ultrapure water,
- sending the ultrapure water to a use point through a feed line,
- treating an object with the ultrapure water at the use point, and
- circulating the resulting spent pure water to the primary-pure-water tank through a return line, which method includes injecting ozone into the spent pure water between the use point and the primary-pure-water tank and supplying a hydrogen-containing gas to the primary pure water between the primary-pure-water tank and the ultrapure-water producing device to conduct residual-ozone removal and oxygen elimination. This invention further provides an apparatus for use in practicing the method.

BRIEF DESCRIPTION OF THE DRAWINGS

In FIG. 2, 24 is a pure-water producing device, 12 is a primary-pure-water tank, 13 is a circulating pump, 15 is a hydrogen spraying device, 16 is a ultrapure-water producing device, 17 is a polisher, 18 is a precision filter, 19 is a feed line, 21 is a use point, 22 is a return line, and 23 is a ozonizer.

FIG. 3 is a flow sheet illustrating the outline of the ozone sterilization of ultrapure water according to a prior art technique.

DETAILED DESCRIPTION OF THE INVENTION

Figure 1:
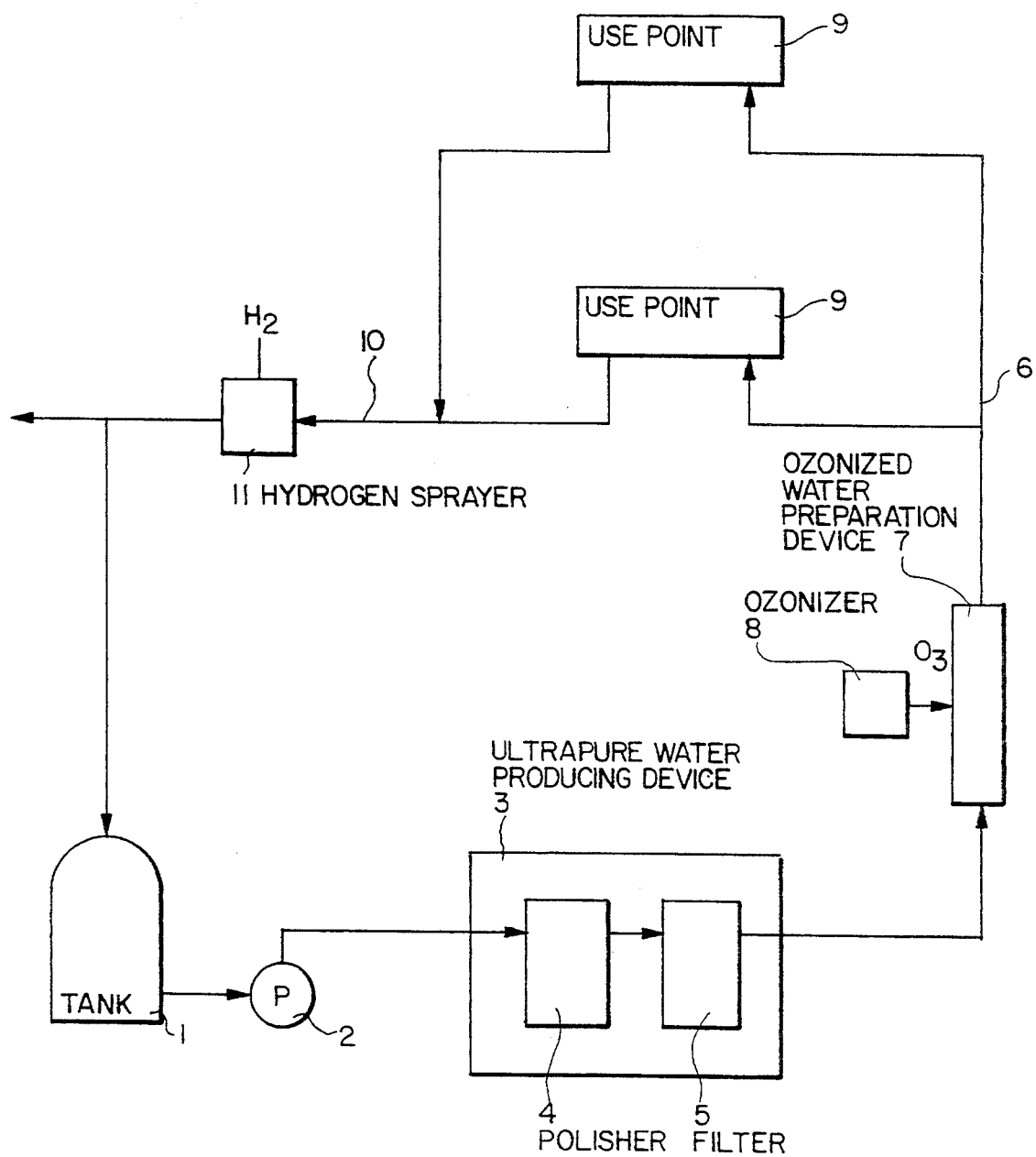
FIG. 1 provides a flow sheet illustrating the system for treatment with ozonized water according to the present invention wherein 1 is a primary-pure-water tank, 2 is a circulating pump, 3 is a ultrapure-water producing device, 4 is a polisher, 5 is a precision filter, 6 is a feed line, 7 is a ozonized-water preparing device, 8 is a ozonizer, 9 is a use point, 10 is a return line, 11 is a hydrogen spraying device.

The present invention will be explained below in greater detail.

Ozone has a higher oxidizing power than chlorine, is effective in sterilization, deodorizing, decoloring, etc., and does not give rise to any problems concerning secondary environmental pollution because it decomposes to oxygen after serving its oxidative function. Hence, the range of ozone utilization is expanding recently, and ozone is used in a variety of fields such as the treatment of water, e.g., semiconductor-cleaning water, and medical and food applications.

The germicidal power of ozone is utilized also in this invention to conduct the sterilization of an ultrapure-water-producing and supplying system and treatments such as cleaning or sterilization of semiconducting substrates and liquid crystals. In the system of this invention for treatment with ozonized water, pure water produced by an ordinary technique, e.g., distillation or ion exchange, is fed to an ultrapure-water producing device containing a polisher and a precision filter to produce ultrapure water having a resistivity close to 18.25 MΩcm, which ultrapure water contains almost no metallic impurities. An ozone-containing gas which usually is a mixture of ozone and oxygen is then injected into and dissolved into the ultrapure water, producing ozonized water (also containing oxygen gas dissolved therein). This ozonized water is fed through a feed line to each use point, where the germicidal function of ozone is utilized in treating semiconducting substrates or other works.

Further, the ultrapure water or pure water comes to contain ozone and, hence, the inside of the system downstream from the injection point is kept in a substantially sterile state and the growth and multiplication of bacteria and other organisms are inhibited therein.

Ozone remains in the spent pure water or unused ultrapure water discharged from the use point (in some cases herein, ultrapure water and pure water are collectively referred to simply as "pure water"). In this invention, the ozone (and oxygen) remaining in the pure water is removed by converting it into water by reaction of ozone and oxygen with hydrogen. The removal of residual ozone (and oxygen) by reaction with hydrogen can be accomplished with a hydrogen spraying device or the like. When the pure water containing ozone and oxygen is sprayed into a hydrogen spraying device packed with a catalyst which catalyzes the reaction of ozone or oxygen with hydrogen in the hydrogen-containing gas to produce water, the ozone and oxygen contained in the pure water react with hydrogen gas and are removed as water. Unlike treatment with active carbon, with this residual-ozone removal using hydrogen gas, there is a lesser tendency for impurities to be included and the sprayed water is converted to pure water which does not contain either ozone or impurities.

Since the ultrapure-water producing device present in the system of this invention has poor resistance to ozone, if the ozone-containing ultrapure or pure water is supplied as it is to the ultrapure-water producing device, the ultrapure water produced by the device has a reduced purity and this results in impaired quality of objects treated with the ultrapure water. Therefore, in an embodiment of the present invention, a hydrogen-containing gas is supplied to the line between the primary-pure-water tank and the ultrapure-water producing device to remove the residual ozone to thereby supply substantially ozone-free pure water to the ultrapure-water producing device.

If the growth of bacteria within the line between this device and the ultrapure-water producing device cannot be inhibited because of the absence of ozone therein, it is desirable to dispose that device immediately before the ultrapure-water producing device so as to minimize the length of the ozone-free line.

If this pure water is discharged as it is, this does not pose an environmental problem because the impurity content of the water is almost zero. The pure water can alternatively be circulated to the ultrapure-water producing device and reused since it does not contain ozone, which adversely affects the ultrapure-water producing device.

The ozone for use in this invention should be high-purity ozone containing substantially no impurities. Although such ozone can be produced by the silent discharge method in which a high voltage is applied to oxygen gas to convert part of the oxygen into ozone, the ozone produced in this method contains a considerable amount of particulate and metallic impurities. Hence, it is undesirable to use ozone produced in this manner especially for cleaning in the electronics industry. In the present invention, it is desirable to use an oxygen-mixed ozone gas obtained using an electrolytic method, by which ozone having a higher purity than that produced by the above-described silent discharge method can be obtained. The ozone gas concentration in the mixed gas is about 14 to 20% by weight.

For obtaining such an oxygen-ozone mixed gas by the electrolysis of pure water, use may be made of a method in which a material comprising an ozone-resistant substrate, e.g., a titanium substrate, covered with lead oxide or tin oxide is disposed as an anode on one side of a solid electrolyte and a material comprising a stainless-steel, carbon, or other substrate covered with a platinum group metal, e.g., platinum, iridium, palladium, osmium, etc. is disposed as a cathode on the other side, and a direct current voltage is applied thereto so that the current flows through the anode and the cathode, while pure water is fed to the anode continuously or intermittently.

It is desirable that in order to effectively conduct sterilization with ozone, the ozone-containing gas should be injected in such an amount that the ozone concentration in the ultrapure water or pure water is about $10 \times 10^{-3}$ to $500 \times 10^{-3}$ mg/l.

Hydrogen gas commercially available in a tank can be used as the hydrogen-containing gas for use in the removal of residual ozone. However, since high-concentration hydrogen gas is obtained at the cathode in the electrolysis described above, it is advantageous to supply hydrogen gas which has been electrolytically produced to the hydrogen spraying device or the like. It is desirable for the ratio of the hydrogen gas supplied to the hydrogen spraying device to the ozone gas injected into the line be kept in the range of from about 2:1 to 5:1 by weight.

One embodiment of the method for treatment with ozonized water according to the present invention is explained below by reference to the accompanying FIG. 1.

FIG. 1 is a flow sheet illustrating one embodiment of the method for treatment with ozonized water according to the present invention.

Primary pure water produced by distillation or ion exchange is stored in a primary-pure-water tank 1. This primary pure water is then fed to an ultrapure-water producing device 3 by means of a circulating pump 2 connected to the tank 1.

The ultrapure-water producing device 3 comprises a polisher 4 and a precision filter 5; inorganic substances present in the pure water are removed by the polisher 4 and are also removed by the filter 5 along with organic substances in particulate or other form which are present in the pure water, thereby producing ultrapure water. An ozone-containing gas produced by an ozonizer 8 adjacent to an ozonized-water preparing device 7 disposed in a feed line 6 is injected into the ultrapure water in the device 7 to convert the ultrapure water to ozonized water. This ozonized water is fed simultaneously to two use points 9 arranged in parallel as shown in FIG. 1. At the use points 9, a treatment, e.g., cleaning of electronic parts, is conducted. The spent pure water resulting from this treatment or the unused ultrapure water that has not been used in this treatment because excess water has been fed, which waters each contains ozone and oxygen, is collected and passed through a return line 10, during which passing the pure water enters a hydrogen spraying device 11 disposed in the line 10 and packed with a catalyst, the pure water comes into contact with a hydrogen-containing gas supplied to the device 11, whereby the residual ozone and oxygen react with the hydrogen and are converted to water and removed. The pure water from which the residual ozone and oxygen have been removed is then circulated to the primary-pure-water tank 1 through the return line 10 and reused, or it is discharged from the system.

The pure water circulated to the primary-pure-water tank 1 is likewise fed to the ultrapure-water producing device 3 by means of the circulating pump 2. Since this pure water is almost free of residual ozone, it does not adversely affect the performance of the ultrapure-water producing device 3. The pure water discharged outside the system also does not pose an environmental or hygienic problem because it contains neither ozone nor oxygen.

Another embodiment of the method for the ozone sterilization of ultrapure water according to the present invention is explained below by reference to the accompanying FIGS. 2 and 3.

Figure 2:
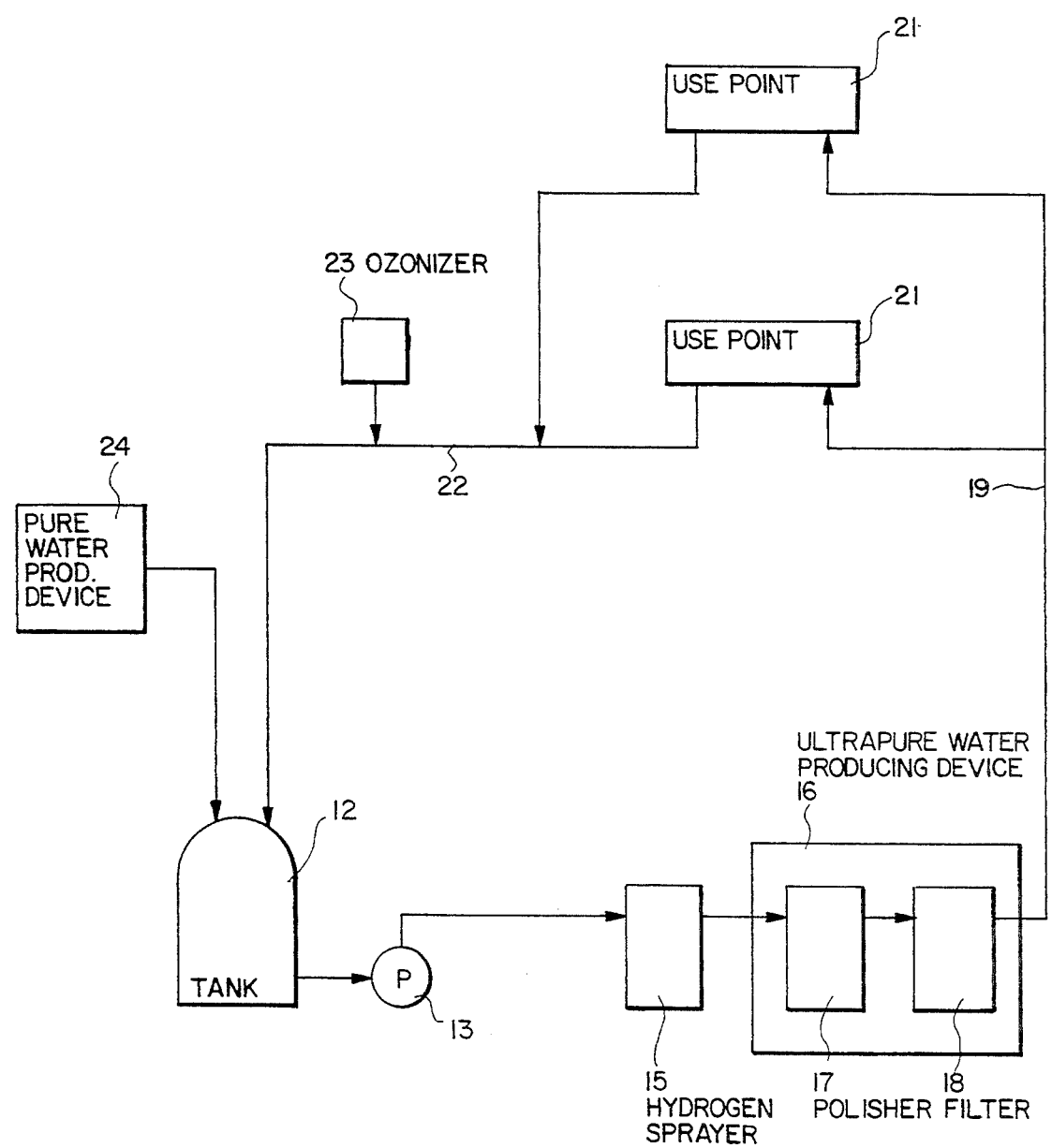
FIG. 2 is a flow sheet illustrating the outline of the ozone sterilization of ultrapure water according to the present invention.

FIG. 2 is a flow sheet illustrating an embodiment of the method for the ozone sterilization of ultrapure water according to the present invention.

Primary pure water produced in a pure-water producing device 24 by distillation or ion exchange is first stored in a primary-pure-water tank 12. This primary pure water is then supplied to an ultrapure-water producing device 16 through a hydrogen spraying device 15 by means of a circulating pump 13 connected to the tank 12.

The ultrapure-water producing device 16 comprises a polisher 17 and a precision filter 18; inorganic substances present in the pure water are removed by the polisher 17 and are also removed by the filter 18 along with organic substances, in particulate or other forms, which are present in the pure water, thereby producing ultrapure water. The ultrapure water is passed through a feed line 19 and fed simultaneously to two use points 21 arranged in parallel in the case shown in FIG. 2. At the use points 21, a treatment, e.g., cleaning of electronic parts, is conducted. The spent pure water resulting from this treatment or the unused ultrapure water which has not been used in this treatment because of excess feeding is collected and circulated to the primary-pure-water tank 12 through a return line 22, during which circulation an ozone-containing gas produced by an ozonizer 23 is injected into the spent pure water or unused ultrapure water present in the return line 22.

The pure water circulated to the primary-pure-water tank 12 is likewise supplied to the hydrogen spraying device 15 by means of the circulating pump 13. Since this hydrogen spraying device 15 is packed with a decomposition catalyst for ozone and oxygen, the ozone and oxygen contained in the pure water supplied to the hydrogen spraying device 15 react with hydrogen to form water and are thus removed from the pure water. The resulting pure water is fed to the ultrapure-water producing device 16.

The treatment of parts with ultrapure water at each use point 21 is conducted by the operations described above. Since an ozone-containing gas is injected by the ozonizer 23 into the pure water in the return line 22, the pure water or ultrapure water circulating through the system contains ozone until it reaches the hydrogen spraying device 15 and, hence, the multiplication of bacteria is inhibited. It is therefore possible to conduct the treatment with substantially bacterium-free ultrapure water at each use point 21.

Examples of the method for treatment with ozonized water according to the present invention and of the ozone sterilization of ultrapure water are given below, but these example are not to be construed as limiting the scope of the present invention. Unless otherwise indicated, parts, percents, ratios and the like are by weight.

EXAMPLE 1

The cleaning treatment of parts with ozonized water was performed according to the flow chart shown in FIG. 1.

Feedstock water having a resistivity of $10^4$ Ωcm was contacted with an anion-exchange resin and a cation-exchange resin in a pure-water producing device to remove impurities, and the resulting pure water having a resistivity of 2 MΩcm was stored in a primary-pure-water tank. This pure water was fed to an ultrapure-water producing device comprising a polisher and a microfilter (pore diameter, 0.1 μm) to produce ultrapure water having a resistivity of 18.2 MΩcm. The ultrapure water had an oxygen concentration of 0.5 ppb. This ultrapure water was fed to an ozonized-water preparing device at a rate of 10 l/min and contacted therein with an ozone-containing gas at a rate of 10 g-$O_3$ per hour to prepare ozonized water. The ozonized water had an ozone concentration of 10 mg/l and a dissolved oxygen concentration of 9 mg/l or higher, i.e., the water contained an oxygen in a supersaturated state.

This ozonized water was fed to use points and used for the cleaning of semiconducting substrates. Thereafter, the ozone concentration of the spent pure water was measured and found to have been reduced to 3 mg/l. However, the dissolved oxygen concentration was 9 mg/l or higher, i.e., the water still contained oxygen in a supersaturated state.

This ozone-containing water was sprayed at a rate of 2.8 l/min into a hydrogen spraying device packed with a catalyst comprising a polypropylene resin support and catalyst metal Pd supported thereon in an amount of 10 mg/cm². The pure water discharged from the hydrogen spraying device had an ozone concentration of zero and the dissolved oxygen concentration thereof had been reduced to 1 ppb.

EXAMPLE 2

The ozone sterilization of ultrapure water was performed according to the flow chart shown in FIG. 2.

Feedstock water having a resistivity of $10^4$ Ωcm was contacted with an anion-exchange resin and a cation-exchange resin in a pure-water producing device to remove impurities, and the resulting water was stored in a primary-pure-water tank. This pure water was fed to an ultrapure-water producing device comprising a polisher and a microfilter (pore diameter, 0.1 μm) to produce ultrapure water. The ultrapure water was further fed to a semiconductor substrate cleaning step, and the resistivity, TOC, bacteria number, ozone concentration, and dissolved oxygen amount before cleaning were determined. The results obtained are shown in Table 1 below. After cleaning with the ultrapure water, an ozone-oxygen mixed gas produced by the electrolysis described hereinabove was injected into the resulting pure water in the return line at a rate of 1 mg/min and this pure water was circulated to the primary-pure-water tank.

At this point in time, the resistivity, TOC, bacteria number, ozone concentration, and dissolved oxygen amount were determined. The results obtained are shown in Table 1 below.

This pure water was sprayed at a rate of 20 ml/min into a hydrogen spraying device packed with a catalyst comprising a polypropylene resin support and catalyst metal Pd supported thereon in an amount of 10 mg/cm². The pure water discharged from the hydrogen spraying device had an ozone concentration of zero.

COMPARATIVE EXAMPLE 1

The ozone sterilization of ultrapure water was performed using the same apparatus as that in Example 2 except that ozone injection and the hydrogen spraying device were omitted. The resistivity, TOC, bacteria number, ozone concentration, and dissolved oxygen amount for the ultrapure water or pure water in the primary-pure-water tank and at the use point were determined. The results obtained are given in Table 1 below.

Table 1 shows that in Example 1 the TOC, dissolved oxygen amount, and bacteria number for the ultrapure water at the use point are considerably reduced.

TABLE 1

|  | Example 2 | | Comparative Example 1 | |
|---|---|---|---|---|
|  | Primary-Pure-Water Tank | Use Point | Primary-Pure-Water Tank | Use Point |
| Resistivity (MΩcm) | 15 | 18.2 | 15 | 18.2 |
| TOC (ppb) | 2 | 2 | 30 | 10 |
| Bacteria Number (per 1000 ml) | 50 | 1 | 500 | 50 |
| Ozone Concentration ($10^{-3}$ mg/l) | 50 | — | — | — |
| Dissolved Oxygen (ppm) | 1 | 0.001 | 0.1 | 0.1 |

In one embodiment of this invention as exemplified by Example 1, the method of the present invention for treatment with ozonized water comprises feeding primary pure water to an ultrapure-water producing device containing at least a polisher to convert the primary pure water to ultrapure water, injecting an ozone-containing gas into the ultrapure water to prepare ozonized water, sending the ozonized water to a use point, using the ozonized water for the treatment, and circulating the resulting spent ozonized water to the ultrapure-water producing device for reuse or discharging the spent water, which method includes supplying a hydrogen-containing gas to the spent ozonized water at a point downstream from the use point to remove residual ozone from the ozonized water by converting it into water. The apparatus of the present invention is one usable for practicing the method.

In this embodiment of the present invention, the residual ozone and oxygen contained in the spent pure water used for treating semiconducting substrates etc. at a use point are removed substantially completely by converting these into water by contact with a hydrogen-containing gas. Hence, even if the resulting spent pure water is discharged outside the system as it is, the environment is not polluted. Further, in the case of circulating this pure water to an ultrapure-water producing device to reuse water, the performance of the ultrapure-water producing device with poor resistance to ozone is not deteriorated by the pure water, because the water is free of residual ozone. It is therefore possible to omit the step for pure-water production, e.g., distillation or ion exchange, and to maintain the continuous cycling of ultrapure-water production/ozonized-water preparation/treatment, without stopping the operation.

Furthermore, since an anode gas and cathode gas evolved in water electrolysis can be employed respectively as the ozone-containing gas and the hydrogen-containing gas for use in this invention and these electrolytically evolved gases have a very low impurity content and are producible in the same electrolytic cell, use of these gases not only is economical but also enables improved purity for the ozonized water and circulating pure water.

In another embodiment of this invention exemplified by Example 2, the method of the present invention for the ozone sterilization of ultrapure water comprises feeding primary pure water from a primary-pure-water tank to an ultrapure-water producing device containing at least a polisher to convert the primary pure water to ultrapure water, sending the ultrapure water to a use point through a feed line, treating an object with the ultrapure water at the use point, and circulating the resulting spent pure water to the primary-pure-water tank through a return line, which method includes injecting an ozone-containing gas into the spent pure water between the use point and the primary-pure-water tank and supplying a hydrogen-containing gas to the primary pure water between the primary-pure-water tank and the ultrapure-water producing device to conduct residual-ozone removal and oxygen elimination. The apparatus of this embodiment of the present invention is one usable for practicing this embodiment.

Therefore, in this embodiment of the present invention, since ozone is present in the ultrapure water or pure water located between the ozone injection part and the hydrogen spraying device disposed downstream therefrom, the growth and multiplication of bacteria and other organisms are prevented and the bacterial concentration in the ultrapure water is kept substantially zero without stopping the operation. Consequently, the objects treated with the ultrapure water have improved quality and the treating ability of ultrapure water is fully exhibited. Moreover, since a hydrogen-containing gas is supplied on the upstream side of the ultrapure-water producing device, which has poor ozone resistance, to remove the residual ozone by converting it to water, the ability of the ultrapure-water producing device to produce ultrapure water in this embodiment is never impaired.

While the invention has been described in detailed with reference to specific embodiments, it will be apparent to one skilled in the art that various changes and modifications can be made to the invention without departing from its spirit and scope.

What is claimed is:

1. A method for treatment with ozonized water which comprises
    feeding primary pure water to an ultrapure-water producing device containing at least a polisher to convert the primary pure water to ultrapure water,
    injecting an ozone-containing gas into the ultrapure water to prepare ozonized water,
    sending the ozonized water to a use point,
    using the ozonized water for the treatment, and
    circulating the resulting spent ozonized water to the ultrapure-water producing device for reuse or discharging the spent water, which method includes supplying a hydrogen-containing gas to the spent ozonized water at a point downstream from the use point to remove residual ozone from the ozonized water.

2. A method as claimed in claim 1, wherein the ozone-containing gas is an anode gas evolved in water electrolysis and the hydrogen-containing gas is a cathode gas evolved in water electrolysis.

3. An apparatus for treatment with ozonized water which comprises:
    a primary-pure-water tank for storing primary pure water,
    an ultrapure-water producing device containing a polisher which device is located downstream from the primary-pure-water tank and serves to convert the primary pure water to ultrapure water, an ozonized-water preparing device disposed downstream of the ultrapure-water producing device for injecting an ozone-containing gas into the ultrapure water to prepare ozonized water, one or more use points disposed downstream of the ozonized-water preparing device where work is treated with the ozonized water fed through a feed line, a return line disposed downstream of the use points for discharging the spent ozonized water resulting from the treatment at the use points or for circulating the spent ozonized water to the primary-pure-water tank, and a hydrogen spraying device disposed in the return line for supplying a hydrogen-containing gas to the ozonized water in the return line to remove residual ozone from the ozonized water.

4. A method for the ozone sterilization of ultrapure water which comprises feeding primary pure water from a primary-pure-water tank to an ultrapure-water producing device containing at least a polisher to convert the primary pure water to ultrapure water, sending the ultrapure water to a use point through a feed line, treating with the ultrapure water at the use point, and circulating the resulting spent pure water to the primary-pure-water tank through a return line, which method includes injecting an ozone-containing gas into the spent pure water between the use point and the primary-pure-water tank and supplying a hydrogen-containing gas to the primary pure water between the primary-pure-water tank and the ultrapure-water producing device to conduct residual-ozone removal and oxygen elimination.

5. A method as claimed in claim 4, wherein the ozone-containing gas is an anode gas evolved in water electrolysis and the hydrogen-containing gas is a cathode gas evolved in water electrolysis.

6. An apparatus for the ozone sterilization of ultrapure water which comprises:

a primary-pure-water tank for storing primary pure water, an ultrapure-water producing device containing a polisher which device is located downstream from the primary-pure-water tank and serves to convert the primary pure water to ultrapure water, one or more use points disposed downstream of the ultrapure-water producing device where an object is treated with the ultrapure water fed through a feed line from the ultrapure-water producing device, a return line disposed downstream of the use points for circulating the spent pure water from the use points to the primary-pure-water tank, an ozone injection means disposed between the use points and the primary-pure-water tank for injecting an ozone-containing gas into the spent pure water between the use points and the primary-pure-water tank, and a hydrogen spraying device disposed between the primary-pure-water tank and the ultrapure-water producing device for supplying a hydrogen-containing gas to the primary pure water to remove the ozone present in the primary pure water and conduct oxygen elimination.

* * * * *